United States Patent
Schmidt et al.

(10) Patent No.: US 8,469,896 B2
(45) Date of Patent: Jun. 25, 2013

(54) METHOD FOR SEGMENTING A CARDIOVASCULAR SIGNAL

(75) Inventors: Samuel Emil Schmidt, Aalborg SO (DK); Claus Graff, Klarup (DK); Johannes Jan Struijk, Terndrup (DK)

(73) Assignee: Acarix A/S, Humlebaek (DK)

( * ) Notice: Subject to any disclaimer, the term of this patent is extended or adjusted under 35 U.S.C. 154(b) by 935 days.

(21) Appl. No.: 12/308,756

(22) PCT Filed: Jun. 26, 2006

(86) PCT No.: PCT/DK2006/000375
§ 371 (c)(1),
(2), (4) Date: Aug. 31, 2009

(87) PCT Pub. No.: WO2008/000255
PCT Pub. Date: Jan. 3, 2008

(65) Prior Publication Data
US 2010/0106038 A1    Apr. 29, 2010

(51) Int. Cl.
*A61B 5/02*    (2006.01)
(52) U.S. Cl.
USPC ............ 600/493; 600/490; 600/528; 600/508
(58) Field of Classification Search
USPC .................................. 600/528, 493, 514, 586
See application file for complete search history.

(56) References Cited

U.S. PATENT DOCUMENTS

| | | | |
|---|---|---|---|
| 2002/0138012 A1* | 9/2002 | Hodges et al. | 600/509 |
| 2005/0222515 A1* | 10/2005 | Polyshchuk et al. | 600/528 |
| 2006/0253040 A1* | 11/2006 | Stergiopoulos et al. | 600/493 |
| 2008/0306365 A1* | 12/2008 | Bunce et al. | 600/323 |

FOREIGN PATENT DOCUMENTS

DE    37 32 122 A1    4/1989

OTHER PUBLICATIONS

Wu, C.H., "On the Analysis and Classification of Heart Sounds Based on Segmental Bayesian Networks and Time Analysis," Journal of Chinese Institute of Electrical Engineering, vol. 4, No. 4, pp. 343-350, Nov. 1997.

Semmlow, J., et al., "Coronary Artery Disease—Correlates Between Diastolic Auditory Characteristics and Coronary Artery Stenoses," IEEE on Biomedical Engineering, vol. BME-30, No. 2, pp. 136-139, Feb. 1983.

Wang, P., et al., "Phonocardiographic Signal Analysis Method Using a Modified Hidden Markov Model," Biomedical Engineering, vol. 35, No. 3, pp. 367-374, Mar. 2007.

Brusco, M., et al., "Development of an Intelligent PDA-based Wearable Digital Phonocardiograph," IEEE on Engineering in Medicine and Biology $27^{th}$ Annual Conference, pp. 3506-3509, Sep. 2005.

(Continued)

*Primary Examiner* — Carl H Layno
*Assistant Examiner* — Jon Eric C Morales
(74) *Attorney, Agent, or Firm* — Jacobson Holman PLLC

(57) ABSTRACT

This invention describes a method for dividing a substantial cycli cardiovascular signal into segments by determining the characteristics of said cyclic signal, wherein each cycle in said signal comprises at least two characteristic segments and wherein the method comprises the steps o identifying segments in a cycle based on prior knowledge of said segment characteristics and the step of verifying said identified segments based on a number of statistical parameters obtained from prior knowledge relating to said cyclic signal. Furthermore, the invention describes a system adapted to perform the above-described method.

12 Claims, 3 Drawing Sheets

OTHER PUBLICATIONS

Durand, L., et al., "Digital Signal Processing of the Phonocardiogram: Review of the Most Recent Advancements," Critical Reviews in Biomedical Engineering, vol. 23, No. 3/4, pp. 163-219, 1995.

Haghighi-Mood, A., et al., "Time-Frequency Analysis of Systolic Murmus," Proceedings of the 1997 IEEE Colloquium, Jan. 1997.

* cited by examiner

METHOD FOR SEGMENTING A CARDIOVASCULAR SIGNAL

This is a national stage of PCT/DK06/000375 filed Jun. 26, 2006 and published in English, hereby incorporated by reference.

FIELD OF THE INVENTION

The present invention relates to methods and systems for dividing a cardiovascular signal into segments and for verifying that the signal has been correctly divided into segments.

BACKGROUND OF THE INVENTION

In the field of data handling and signal processing a signal is often recorded/registered by a transducer, and the signal is thereafter digitalized by an A/D converter. The recorded and digitalized signal would typically be used for analysis and/or statistical information.

Auscultation is an example of a technique where a transducer is used to record/register a physical phenomenon, and where the signal is used for analysis and/or statistics. Auscultation is the technical term for listening to the Internal sounds of the body. Auscultation is normally performed for the purposes of examining the cardiovascular system and respiratory systems (heart and lung sounds) as well as the gastrointestinal system (bowel sounds). The sounds are often recorded from a patient by a microphone, A/D converted and stored as a digital file for later analysis in order to diagnose the patient.

In many applications only a part of the recorded signal is used in the analysis. A particular part of the signal could namely be used to extract special parameters that could be used to diagnose the patient. For instance, the lung sounds due to respiration comprise a part where the patient breaths in and a part where the patient breaths out. Both parts of the lung sounds could be used to extract parameters with diagnostic value, however, it is not certain that the parameters could be used for the same diagnose, and it is not certain that it would be the same parameters. Another example could be the heart sounds that comprise two major parts; namely a systolic and a diastolic part. Both parts reflect the cardiac cycle, and the systolic part is the part of the cardiac cycle in which the heart muscle contracts, forcing the blood into the main blood vessels, and the diastole is the part of the heart cycle during which the heart muscle relaxes and expands. During diastole, blood fills the chambers. Both parts of the sound could provide clinicians and other medical professionals with parameters that could be used to diagnose the patient.

In many applications it is therefore necessary to divide the signal into segments in order to perform data handling on the particular segments. Typically the signal is divided into segments using a periodic segmentation where the signal is e.g. divided into segments corresponding to a number of samples or a given time period. This method assumes that the recorded signal is 100% periodical; otherwise the different segments would overlap and thus not be separated properly. Another way of dividing a signal into segments is to find special characteristic(s) in the signal and simply divide the signal into segments using these special characteristic(s). However, it can be difficult to find these special characteristic(s) when the signal to noise ratio of the signal is often very bad, and the segmentation would therefore often fail.

Another problem when dividing a signal into segments is the fact that the individual segments might contain a lot of noise and therefore might be unusable for further data handling.

A consequence of the existing segmentation methods is that wrong or noisy segments are often used for further data handling. The consequence of this could be crucial, especially if the segments are used for diagnostic purpose as is the case in auscultation.

OBJECT AND SUMMARY OF THE INVENTION

The object of the present invention is to solve the above-mentioned problems.

This is achieved by a method for dividing a substantial cyclic cardiovascular signal into segments by determining the characteristics of said cyclic signal, wherein each cycle in said signal comprises at least two characteristic segments, and wherein the method comprises the steps of identifying segments in a cycle based on prior knowledge of said segment characteristics, and the step of verifying said identified segments based on a number of statistical parameters obtained from prior knowledge relating to said cyclic signal. It is hereby achieved that a substantial cyclic cardiovascular signal could be divided into sub-segments, and these sub-segments would thereafter be verified so that only correct segments would be used in a further data handling process. Furthermore, noisy segments could be discarded so that they are not included in further data handling or analysis. A substantial cyclic cardiovascular signal comprises segments that are periodical altered so that the cycles in the cardiovascular signal comprise the same segments, however, the cardiovascular cycles are not 100% cyclic since each cycle may differ due to e.g. noise or the fact that the duration of the diastole may vary due to the physical conditions of the heart. The cardiovascular signal would first be divided into segments based on prior knowledge of the signal. Prior knowledge could e.g. be the fact that a cardiovascular signal comprises two major alternating segments, namely the systolic segment and the diastolic segment; it could be knowledge about the time duration of the different segments; it could be knowledge about the frequency components of the different segments; it could be knowledge about the energy in the different components, etc. Thereafter the segments are verified using statistical parameters obtained from prior knowledge about the cardiovascular signal such as probabilities describing different conditions of each segment. For Instance, if the duration of a segment is longer than a given period of time, it would most likely be a certain type of segment; if the dominating frequency component is within a certain frequency band it could indicate that the segment is of a certain type; the energy level of a segment could also provide statistical information about the segment, etc. Furthermore, it is possible to verify a "train" of segments comprising a number of the cyclic segments. In this way it is possible to both divide the cardiovascular signal into segments and at the same time verify that a "train" of segments is correct.

In another embodiment of the method, the verification comprises the step of calculating the probability that said identified segments are at least one predetermined type defined from prior knowledge of said segment using said statistical parameters. Hereby each segment could be verified by calculating the probability that a segment is a predetermined type such that high probability would indicate that the segments are of the predetermined type. The consequence is that the probability of a segment in a cardiovascular signal being either a diastolic or a systolic segment could be calculated. High probability would therefore indicate that the cardiovascular signal is divided into correct segments. Furthermore, the probability of a "train" of segments could be calculated, and in this way an entire train could be verified.

In another embodiment of the method, the step of calculating the probability that said identified segments are at least one predetermined type defined from prior knowledge is based on a Bayesian network. Hereby the probability of the segments could be calculated based on a number of interrelated statistical parameters.

In another embodiment of the method, at least one of said statistical parameters characterizes said identified segments in the frequency domain. Hereby the frequency components in a segment could be used to verify the segment.

In another embodiment of the method, said identification of segments in a cycle comprises the step of extracting cyclic parameters of said signal. Hereby it is achieved that the cardiovascular segments could be divided into segments based on a number of cyclic parameters extracted from the signal. This could e.g. be embodied by taking an autocorrelation of the cardiovascular signal and thereby identify the duration of cyclic segments in the signal.

In another embodiment of the method, said cyclic cardiovascular signal is a cardiovascular sound. Hereby it is achieved that a cardiovascular sound could be divided into segments, and the segments could be verified as described above. The cardiovascular sound could be recorded using a digital stethoscope.

The invention further relates to a system for dividing a substantial cyclic cardiovascular signal into segments by determining the characteristics of said cyclic signal, wherein each cycle in said signal comprises at least two characteristic segments and wherein said system comprises processing means adapted to Identify segments in a cycle based using prior knowledge of said segment characteristics, verification means adapted to verifying said identified segments based on a number of statistical parameters obtained from prior knowledge relating to said cyclic signal. Hereby it is achieved that the above-described method could be implemented in a system, e.g. as a client/server system, where a server is adapted to receive a cardiovascular signal from a client, the server would hereafter divide the cardiovascular signal into segments using the above-described method and finally send the result back to the client. Such a system could also be a digital stethoscope adapted to record a cardiovascular sound; the stethoscope could thereafter divide the cardiovascular sound segment into segments and further be adapted to perform an analysis of the segments. This analysis could for instance be a diagnosis based on the cardiovascular sound.

In an embodiment of the system, the verification means comprise means adapted to calculate the probability that said identified segments are at least one predetermined type defined from prior knowledge of said segment using said statistical parameters. Hereby the above-described advantages are achieved.

In an embodiment of the system, the means for calculating the probability that said identified segments are at least one predetermined type defined from prior knowledge are further adapted to be using a Bayesian network. Hereby the above-described advantages are achieved.

In an embodiment of the system, at least one of said statistical parameters characterizes said identified segments in the frequency domain. Hereby the above-described advantages are achieved.

In an embodiment of the system, the means for identification of segments in a cycle comprise means for extracting cyclic parameters of said signal. Hereby the above-described advantages are achieved.

In an embodiment of the system, said cyclic signal is a cardiovascular sound. Hereby the above-described advantages are achieved.

The invention also relates to a computer-readable medium having stored therein instructions for causing a processing unit to execute a method according to the above. Hereby the method could be implemented in a data processor unit and the above advantages would be achieved.

DESCRIPTION OF EMBODIMENTS

Figure 1:
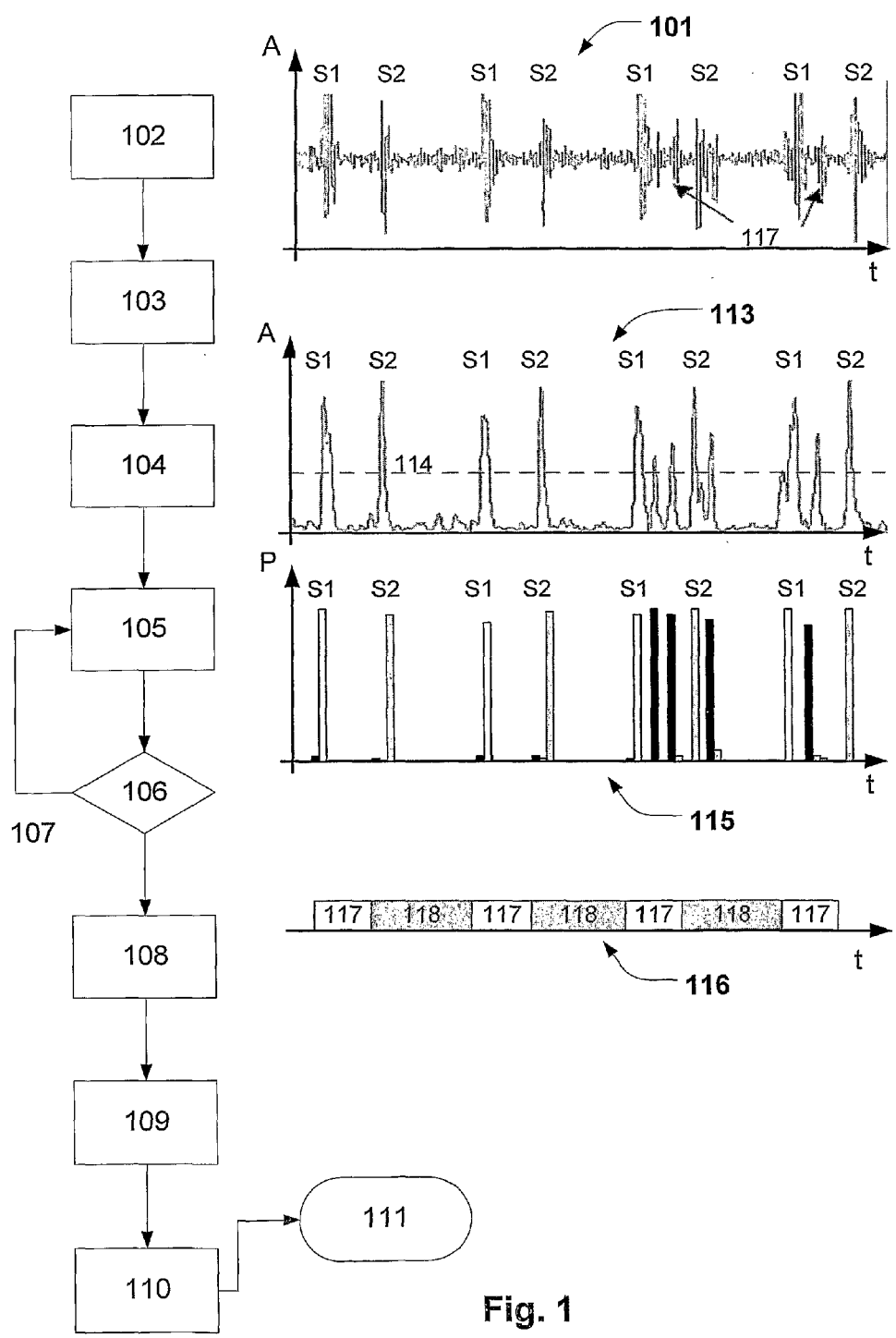
FIG. 1 illustrates a flow diagram of the segmentation method according to the present invention.

FIG. 1 illustrates a flow diagram of the segmentation method according to the present invention used to automatically divide a heart sound (101) into sub-segments. The heart sound (101) has been recorded by a stethoscope and the signal has been digitized in order to digitally process the signal. The graph shows the amplitude (A) of the sound intensity as a function of time (t). The heart sounds reflect events in the cardiac cycle, i.e. the deceleration of blood, turbulence of the blood flow and the closing of valves. The closing of the valves are typically represented by two different heart sounds, the first (S1) and the second (S2) heart sound. The first and second heart sounds are illustrated in the figure, and (S1) marks the beginning of systole, which is the part of cardiac cycle in which the heart muscle contracts, forcing the blood Into the main blood vessels, and the diastole, which is the part of the heart cycle during which the heart muscle relaxes and expands. During diastole, blood fills the heart chambers. In contrast (S2) marks the beginning of a diastole and the end of a systole. Some part of the sound could also contain noise peaks (117).

The purpose of the segmentation method is to classify the recorded heart sound into systolic, diastolic and noise segments. The illustrated method includes steps of noise reduction (102) followed by envelope creation (103). The noise reduction could be implemented as a high-pass filer followed by removal of high amplitude friction noise spikes due to external noise like movement of the stethoscope during recording and thereafter a low pass filter. The purpose of the envelope creation is to enhance the trend of the signal. The envelope is in this embodiment created by calculating the Shannon energy of the signal:

$$se(n) = -x(n)^2 \cdot \log x(n)^2$$

where x is the signal and se is the Shannon energy. The high amplitude components in the signal are weighted higher than low amplitude components when calculating the Shannon energy. The envelope (113) of the heart sound (101) calculated by using the Shannon energy is shown in figure (113), and it can be seen that the contour of the heart sounds S1 and S2 are enhanced.

In order to classifying the detected sounds into systolic segments, diastolic segments and noise components based on interval durations on either side of the heart sounds S1 and S2, it is necessary to know how long the intervals between S1's and S2's are. Therefore, the durations of the heart cycles (systolic and diastolic intervals) are extracted from an autocorrelation of the envelope (104). This process is described in more detail in FIG. 2.

Candidate S1's and S2's are then detected (105) using the time intervals extracted above and a threshold (114) on the envelope (113). To reduce the number of detected noise spikes, a minimum requirement is applied to the candidate segments which effectively remove some of the erroneously detected noise spikes. In some recordings there is a large difference between the intensity of S1 and S2 sounds. This causes a problem since some of the low intensity sounds may be missed by the threshold. As a result, the segmentation method performs a test for missing S1 and S2 sounds (106). If it can be determined that some segments are missing the threshold procedure is rerun (107) using lower local thresholds.

Once the signal has been divided into segments as described above, interval parameters and frequency parameters for each segment are then extracted (108). The parameters aid in the classification of the sounds into systolic and diastolic segments.

The interval parameters are four Boolean parameters extracted for each sound by comparing the time duration to the previous sound and to the next sound with the time intervals extracted using the autocorrelation. The parameters are as follows:

AfterDia: is true if the sound is succeeded by a second sound after a period corresponding to the duration of a diastole AfterSys: is true if the sound is succeeded by a second sound after a period corresponding to the duration of a systole BeforeDia: is true if the sound follows a second sound after a period corresponding to the duration of a diastole BeforeSys: is true if the sound follows a second sound after a period corresponding to the duration of a systole.

The frequency parameter divides the sounds into low frequency and high frequency sounds by calculating the median frequency of the sound. This is useful information since the first heart sound is expected to be a low frequency sound and the second heart sound is expected to be a high frequency sound.

The parameters are passed into a Bayesian network where the probability of a segment being a S1, S2 and noise sound is computed (109). The figure illustrates a bar chart (115) of the probability calculated for each sound in the heart signal (101). Each sound would typically have one dominating probability indicating the type (S1, S2 or noise) of the sound. Thereby all sounds are classified into S1, S2 and noise sounds. However, the probability of the three types would in some cases be more or less equal, and In that case it is not possible to classify the sound into a S2, S2 or noise sound using the Bayesian network.

The probabilities are used in the last step (110) to divide and verify the heart signal into systole and diastole segments. This is done by using the position of the identified S1 and S2 sounds to mark the beginning of a systolic and diastolic sound segment respectively.

The final results of the method (111) are the beginnings and ends of all Identified systoles and diastoles. Therefore a "train" (116) of alternating systoles (117) and diastoles (118) can be created. Once the systoles and diastoles have been identified they can be used in further data handling, e.g. to extract further parameters from these segments and subsequently use the parameters to classify the medical condition of the recorded heart sound.

FIG. 2 illustrates the relationship between the envelope autocorrelation and the cardiac cycle, and how the intervals between heart sounds S1 and S2 can be found from the autocorrelation.

Figure 2A:
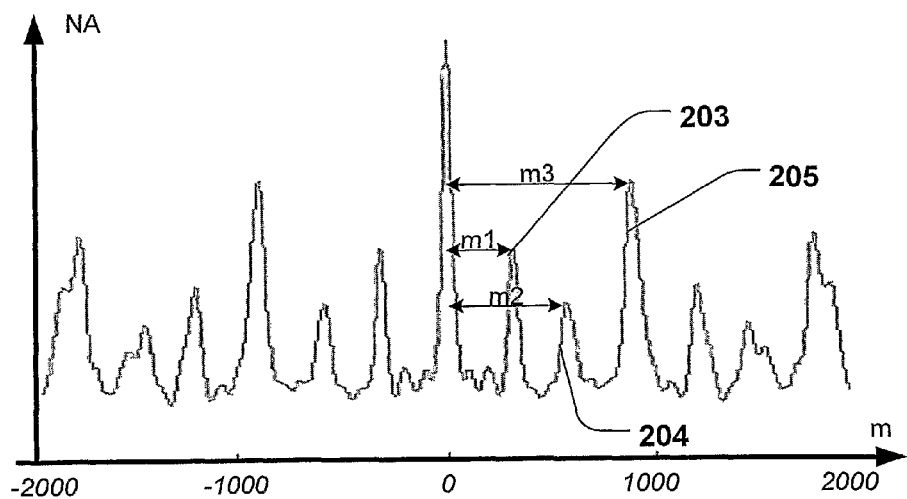
FIG. 2 illustrates the relationship between the envelope autocorrelation of a cardiovascular sound signal and the cardiac cycle.

FIG. 2a illustrates the envelope autocorrelation with the normalized autocorrelation at the y-axis (NA) and the displacement (m) of the shifted envelope at the x-axis.

Figure 2B:
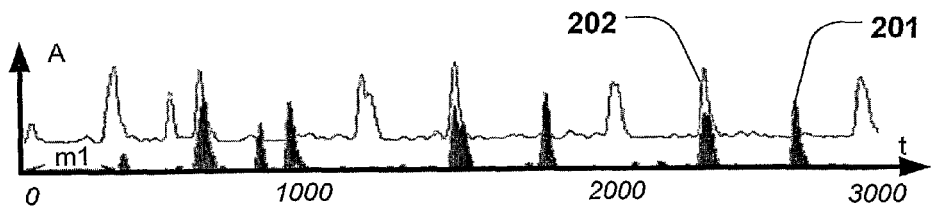

FIG. 2b illustrates the displacement (m1) when the shifted envelope (201) is displaced by the duration of the systole corresponding to the unshifted envelope (202). The y-axis shows the amplitude (A) of the envelope and the x-axis the time (t). The S1's in the displaced envelope are multiplied by the S2's in the unshifted envelopes resulting in the first peak (203) seen in the autocorrelation.

Figure 2C:
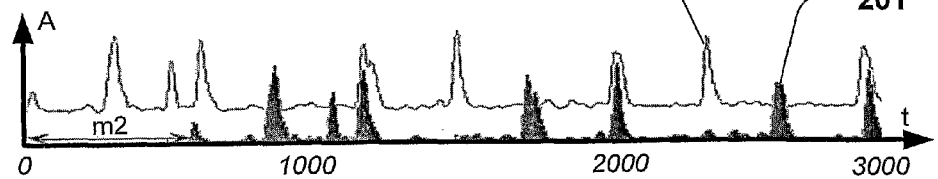
Figure 2D:
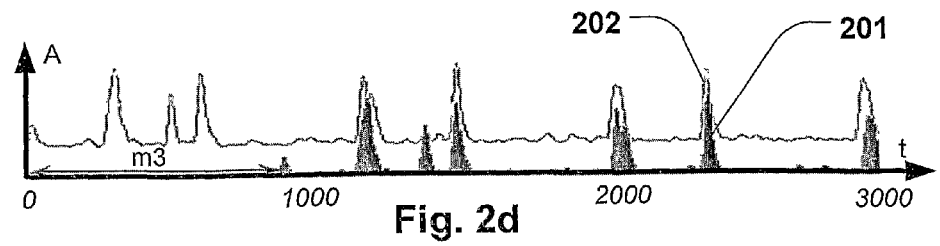

FIG. 2c illustrates the displacement (m2) when the shifted envelope (201) is displaced by the duration of the diastole corresponding to the unshifted envelope (202). The displaced S2's are multiplied by the S1's in the unshifted envelope resulting in the second peak (204) seen in the autocorrelation.

FIG. 2b illustrates the displacement (m3), when the shifted envelope (201) is displaced by the duration of the cardiac cycle corresponding to the unshifted envelope (202). The S1's in the displaced envelope are multiplied by the S1's In the unshifted envelope and the S2's in the displaced envelope are multiplied by the S2's in the unshifted envelope. When this occurs the dominating peak (205) in the autocorrelation is produced.

The interval between the heart sounds could therefore be found by measuring the distance between the peaks in the autocorrelation as described above.

Figure 3:
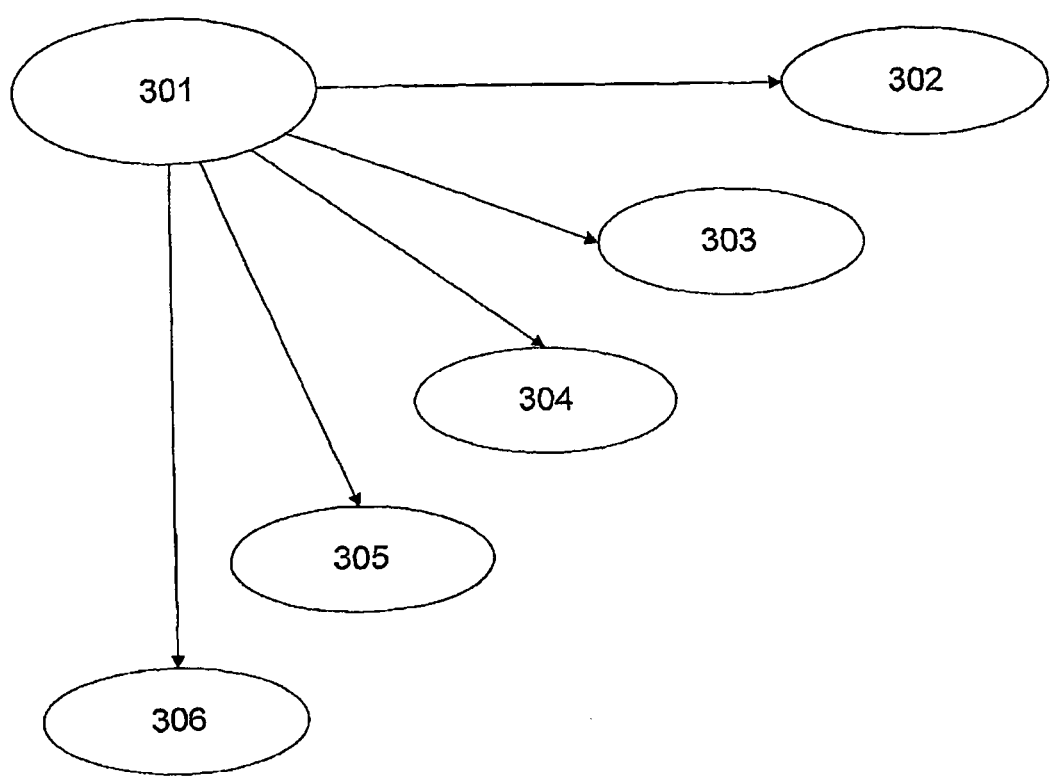
FIG. 3 illustrates an implementation of the Bayesian network used in the present invention.

FIG. 3 illustrates the implementation of the Bayesian network used to calculate the probability of a sound of being an S1, S2 and noise sound in step (109). The basic concept In the Bayesian network is the conditional probability and the posterior probability. The conditional probability describes the probability of the event a given the event b.

$$P(a|b) = x_o \qquad [3.1]$$

If the above equation describes the initial conditional probability, the posterior probability would be:

$$P(b|a) = x_p \qquad [3.2]$$

According to Bayes' rule the relation between the posterior probability and the conditional probability is:

$$P(b|a) = \frac{P(a|b)P(b)}{P(a)} \qquad [3.3]$$

where $P(a)$ is the prior probability for the event a, and $P(b)$ is the prior probability for the event b. Equation [3.3] only describes the relation between one parent and one child, but since the event a can be the combination of several events $\{a_1, a_2, \ldots, a_n\}$ the equation can be expanded to:

$$P(b|a_1, a_2, \ldots, a_n) = \frac{P(a_1, a_2, \ldots, a_n|b)P(b)}{P(a_1, a_2, \ldots, a_n)} \qquad [3.4]$$

Since the goal is to find the probability for the different states of b when $a_1$ and $a_2$ are known, $P(a_1, a_2, \ldots, a_n)$ is Just a normalizing constant k and [3.4] can be simplified to:

$$P(b|a_1, a_2, \ldots, a_n) = k \cdot P(a_1, a_2, \ldots, a_n|b)P(b) \qquad [3.5]$$

If child events $(a_1, a_2, \ldots, a_n)$ are conditionally independent, equation [3.5] can be generalized to:

$$P(b \mid a_1, a_2, \ldots, a_n) = k \cdot P(b) \prod_{i=1}^{N} P(i \mid b) \quad [3.6]$$

where N is the number of known events a. Equation [3.6] is useful for determining the probability of the event b if the states of all a events are known, and If all a events are conditionally independent. A Bayesian network based on equation [3.6] is called a naive Bayesian network as it requires conditional independency of the children.

The task for the Bayesian network is to evaluate the type of each detected sound above the detection threshold. For each of these sounds, the posterior probability of being an S1 sound, an S2 sound or a noise component is calculated and the Bayesian network is constructed using one parent and five children. The parent is a sound above the envelope threshold (301) and the children are the five parameters described above: Frequency (302), AfterSys (303), AfterDia (304), BeforeSys (305) and BeforeDia (306). When determining the posterior probability for the type of a particular sound, the prior probability for the different states of a sound type P(S) and the conditional probabilities must be known, i.e. the conditional probabilities that "AfterSys" is in a given state when S is a given type, P(AfterSys|S). This posterior probability requires a definition of P(S), P(AfterSys|S), P(AfterDia|S), P(BeforeSys|S), P(BeforeDia|S) and P(Frequency|S) before the equation [3.6] can be used to calculate the posterior probability of a sound being a particular type of sound.

The prior probability that a sound is an S1, S2 or a noise component changes between recordings. In the optimal recording, where no noise components are detected, the prior probability for noise is zero, $P(S_{=Noise})=0$. If this is the case and an equal number of S1's and S2's are detected, the prior probability that the detected sound is an S1 is 50%, and similar for S2. Therefore $P(S_{=S1})=P(S_{=S2})=0.5$ if $P(S_{=noise})=0$. However, this optimal condition can not be assumed for real signals, and noise sounds would be detected. This will increase the prior probability that a given sound is noise.

The exact probability of a detected sound being noise, $P(S_{=noise})$, can be defined if the number of detected noise sounds, $N_{noise}$, and the total number of detected sounds, $N_{sounds}$, are known. For Instance, If it is known that four noise sounds are detected, $N_{noise}=4$, and the total number of detected sounds is 20, the probability that the sound being examined is a noise sound is $P(S_{noise})=4/20$. However, in most signals $N_{noise}$ is unknown and an estimate of $N_{noise}$ is therefore necessary, and this estimate can be based on already available information since the duration of a heart cycle is known from the envelope autocorrelation (104). The expected number of cardiac cycles in one recording can therefore be calculated by dividing the length of the recording with the length of the cardiac cycles. The number of S1's and S2's In a recording is therefore twice the number of cardiac cycles in a recording. The prior probability of the sound type would therefore be:

$$P(S_{=noise}) = \frac{N_{noise}}{N_{sound}} \quad [3.7]$$

and the prior probability that the detected sound is an S1 or S2:

$$P(S_{=s1}) = P(S_{=s2}) = \frac{1 - P(S_{=noise})}{2} \quad [3.8]$$

The conditional probability that an S1 is followed by an S2 sound after an interval corresponding to the duration of a systole, $P(\text{AfterSys}|S_{=S1})$, depends on several factors. The S1 sounds will normally be followed by S2 sounds after an interval of duration equal to the systole. Deviations from this can also occur, for instance when S1 is the last sound in the recording, or if S2 is missing because it is not detected by the threshold. It may also occur that a weak (below threshold) S2 is detected because noise occurs in the tolerance window associated with those sounds. The probability that "AfterSys" is false if the sound is an S1 sound may thus be calculated as $$P(\text{AfterSys}_{=false}|S_{=S1})=P(\text{EndSound}\cup\text{Singlesound}, \text{NoiseInWin}) \quad [3.9]$$

where "EndSound" is an event describing that the sound is the last sound in the recording. "SingleSound" describes that S1 is not followed by S2 since the next S2 sound is not detected due to sub-threshold amplitude. "NoiseinWin" describes noise occurrence in the window where the S2 sound was expected. The conditional probability that "AfterSys" is true given that the examined sound is an S1 sound is given by:

$$P(\text{AfterSys}_{=true}|S_{=S1})=1-P(\text{AfterSys}_{=false}|S_{=S1}) \quad [3.10]$$

If the examined sound is an S2 sound it is not likely that any sound occurs after an interval corresponding to the systolic duration since the next S1 sound will occur after the duration of the diastole. An exception is if a noise sound occurs in the window P(NoiseInWin) or if the systole and diastole durations are equal. If the duration of the diastole is equal to the duration of the systole the S1 sound which follows the S2 sound after the duration of a diastole occurs in both the systole tolerance window and in the diastole tolerance window. This will happen if the heart rate of the subject is high. The probability, that a sound occurs in both tolerance windows (overlap) is equal to the degree of the overlap between the systole and diastole tolerance window. This probability is termed P(Overlap). Therefore, the conditional probability that a sound occurs in the window after systole duration if the examined sound is an S2 sound is:

$$P(\text{AfterSys}_{=true}|S_{=S2})=P(\text{Overlap}\cup\text{NoiseInWin}) \quad [3.11]$$

The conditional probability that a sound does not occur after a systole duration, if the examined sound is an S2, is the opposite of the conditional probability that it does occur:

$$P(\text{AfterSys}_{=false}|S_{=S2})=1-P(\text{AfterSys}_{=true}|S_{=S2}) \quad [3.12]$$

The conditional probability that a detected noise sound is followed by another sound after the systole duration is based on the probability that a sound of any kind is present in a segment with the length of the used tolerance window. This can be estimated from the ratio of the tolerance window length multiplied by the number of detected sounds minus one to recording length.

$$P(\text{SoundInWin}|S_{=S2})=1-P(\text{AfterSys}_{=true}|S_{=S2}) \quad [3.12]$$

The conditional probability that a detected noise sound is followed by another sound after the systole duration, $P(\text{AfterSys}|S_{=noise})$, is based on the probability that a sound of any kind is present in a segment with the length of the used tolerance window. This can be estimated from the ratio of the tolerance window length multiplied by the number of detected sounds minus one to recording length. The conditional probability that a noise sound is followed by another sound after a systole duration is therefore:

$$P(AfterSys_{=true} | S_{=noise}) = P(SoundInWin) \quad [3.13]$$
$$= \frac{(N_{sound} - 1) \cdot 2 \cdot Sys_{tot}}{RecLength}$$

where $N_{sound}$ is the number of sounds within the recording, $Sys_{tot}$ is the duration of a systole and RecLength is the length of the recording. The conditional probability that a noise is not followed by another sound after the systole interval is opposite:

$$P(AfterSys_{=false}|S_{=noise})=1-P(SoundInWin) \quad [3.14]$$

The conditional probabilities for P(AfterDia|S), P(BeforeSys|S) and P(BeforeDia|S) are based on the same assumptions used to define P(AfterSys|S). These conditional probabilities can be found In the tables below:

|  | False | True |
|---|---|---|
| P(AfterSys|S) |  |  |
| S1 | P((EndSound ∪ SingleSound), NoiseInWin) | 1 − P((EndSound ∪ SingleSound), NoiseInWin) |
| S2 | 1 − P(Overlap ∪ NoiseInWin) | P(Overlap ∪ NoiseInWin) |
| Noise | 1 − P(SoundInWin) | P(SoundInWin) |
| P(AfterDia|S) |  |  |
| S1 | 1 − P(Overlap ∪ NoiseInWin) | P(Overlap ∪ NoiseInWin) |
| S2 | P((EndSound ∪ SingleSound), NoiseInWin | 1 − P((EndSound ∪ SingleSound), NoiseInWin) |
| Noise | 1 − P(SoundInWin) | P(SoundInWin) |
| P(AfterSys|S) |  |  |
| S1 | 1 − P(Overlap ∪ NoiseInWin) | P(Overlap ∪ NoiseInWin) |
| S2 | P((EndSound ∪ SingleSound), NoiseInWin | 1 − P((EndSound ∪ SingleSound), NoiseInWin) |
| Noise | 1 − P(SoundInWin) | P(SoundInWin) |
| P(AfterDia|S) |  |  |
| S1 | P((EndSound ∪ SingleSound), NoiseInWin) | 1 − P((EndSound ∪ SingleSound), NoiseInWin) |
| S2 | 1 − P(Overlap ∪ NoiseInWin) | P(Overlap ∪ NoiseInWin) |
| Noise | 1 − P(SoundInWin) | P(SoundInWin) |

It has previously been found that the frequency parameter classified 86% of the S1 sounds as low frequent and 80% of the S2 sounds as high frequent. 85% of all noise sounds were classified as high frequent. This information was used as the conditional probabilities between the frequency parameter P(Frequency|S):

| P(Frequency|S) | Low | High |
|---|---|---|
| S1 | 0.86 | 0.14 |
| S2 | 0.20 | 0.80 |
| Noise | 0.15 | 0.85 |

When all conditional probabilities are found, equation [3.6] is used by the Bayesian network to calculate the posterior probabilities for all detected sounds. This way, three probabilities are calculated for each sound that reflect how likely it is that the current sound is a given type.

It should be noted that the above-mentioned embodiments rather Illustrate than limit the invention, and that those skilled in the art will be able to suggest many alternative embodiments without departing from the scope of the appended claims.

The invention claimed is:

1. A method for dividing a substantial cyclic cardiovascular signal into segments by determining the characteristic of said cyclic signal, wherein each cycle in said signal comprises at least two characteristic segments and wherein the method comprises the steps of:
   providing a substantially cyclic cardiovascular signal obtained from a patient;
   identifying at least two characteristic segments in a cycle of said cardiovascular signal based on prior knowledge of said segments' characteristics;
   verifying said identified segments based on a number of statistical parameters obtained from prior knowledge relating to said cyclic signal, said verifying including the step of calculating a probability that said identified segments are at least one predetermined type defined from prior knowledge of said segments using said statistical parameters;
   said step of calculating the probability that said identified segments are at least one predetermined type defined from prior knowledge is based on Bayesian statistics; and
   using information relating to the verified segments to directly or indirectly diagnose the patient.

2. The method according to claim 1, wherein at least one of said statistical parameters characterizes said identified segments in the frequency domain.

3. The method according to claim 1, wherein said identification of segments in a cycle includes the step of extracting cyclic parameters of said signal.

4. The method according to claim 1, wherein said cyclic cardiovascular signal is a cardiovascular sound.

5. The method as set forth in claim 1, further comprising the step of obtaining the cardiovascular signal from the patient using a stethoscope.

6. A system for dividing a substantial cyclic cardiovascular signal into segments by determining the characteristic of said cyclic signal, each cycle in said signal including at least two characteristic segments, said system comprising:

a receiving unit configured to receive a substantially cyclic cardiovascular signal obtained from a patient;

a processing unit configured to identify at least two characteristic segments in a cycle of said cardiovascular signal based on prior knowledge of said segments' characteristics;

a verification unit configured to verify said identified segments based on a number of statistical parameters obtained from prior knowledge relating to said cyclic signal, said verification unit including a calculating unit configured to calculate the probability that said identified segments are at least one predetermined type defined from prior knowledge of said segments using said statistical parameters, said calculating unit calculating the probability that said identified segments are at least one predetermined type defined from prior knowledge using Bayesian statistics; and an output unit configured to provide information relating to the verified segments to a clinician or other medical professional to assist in directly or indirectly diagnosing the patient.

7. The system according to claim 6, wherein at least one of said statistical parameters characterizes said identified segments in the frequency domain.

8. The system according to claim 6, wherein said processing unit is further configured to extract cyclic parameters of said signal.

9. The system according to claim 6, wherein said cyclic signal is a cardiovascular sound.

10. The system according to claim 6, wherein said receiving unit includes a digital stethoscope.

11. A non-transitory computer-readable medium having stored therein instructions for causing a computer processing unit to divide a substantial cyclic cardiovascular signal input to said processing unit into segments by determining the characteristic of said cyclic signal, wherein each cycle in said signal comprises at least two characteristic segments, said computer processing unit being configured to identify at least two characteristic segments in a cycle of said cardiovascular signal based on prior knowledge of said segments' characteristics, and to verify said identified segments based on a number of statistical parameters obtained from prior knowledge relating to said cyclic signal in order to directly or indirectly diagnose a patient, said verifying including calculating a probability that said identified segments are at least one predetermined type defined from prior knowledge of said segments using said statistical parameters, said calculating being based on Bayesian statistics.

12. A system for dividing a substantial cyclic cardiovascular signal into segments by determining the characteristic of said cyclic signal, each cycle in said signal including at least two characteristic segments, said system comprising:

a receiving unit configured to receive a substantially cyclic cardiovascular signal obtained from a patient;

a processing unit configured to identify at least two characteristic segments in a cycle of said cardiovascular signal based on prior knowledge of said segments' characteristics;

a verification unit configured to verify said identified segments based on a number of statistical parameters obtained from prior knowledge relating to said cyclic signal; and an output unit configured to provide information relating to the verified segments to a clinician or other medical professional to assist in directly or indirectly diagnosing the patient, wherein said system is embodied as a server-client system, said server configured to receive the cardiovascular signal and including the processing, verification and output units, said client configured to receive the information relating to the verified segments sent to the client from the server to assist in directly or indirectly diagnosing the patient.

* * * * *